(12) United States Patent
Hudack et al.

(10) Patent No.: US 7,651,746 B2
(45) Date of Patent: Jan. 26, 2010

(54) HALOGENATED BISDIARYLAMINOPOLYCYCLIC AROMATIC COMPOUNDS AND POLYMERS THEREOF

(75) Inventors: Michelle L. Hudack, Grand Blanc, MI (US); Wanglin Yu, Midland, MI (US); Michael Inbasekaran, Palatine, IL (US); Weishi Wu, Midland, MI (US); Dean M. Welsh, Midland, MI (US); James J. O'Brien, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/579,215

(22) PCT Filed: Nov. 3, 2004

(86) PCT No.: PCT/US2004/036707

§ 371 (c)(1),
(2), (4) Date: Sep. 22, 2006

(87) PCT Pub. No.: WO2005/049546

PCT Pub. Date: Jun. 2, 2005

(65) Prior Publication Data

US 2007/0126345 A1    Jun. 7, 2007

(51) Int. Cl.
*C07C 211/00* (2006.01)
*B41M 5/00* (2006.01)
(52) U.S. Cl. .................................. 428/32.23; 568/337
(58) Field of Classification Search .................. 564/337; 428/32.23
See application file for complete search history.

(56) References Cited

U.S. PATENT DOCUMENTS

| | | | |
|---|---|---|---|
| 4,853,308 A | 8/1989 | Ong et al. | |
| 4,983,482 A | 1/1991 | Ong et al. | |
| 5,879,821 A | 3/1999 | Hsieh | |
| 5,932,383 A * | 8/1999 | Nakata et al. | 430/58.75 |
| 6,169,163 B1 | 1/2001 | Woo | |
| 6,309,763 B1 | 10/2001 | Woo et al. | |
| 2003/0157364 A1 | 8/2003 | Senoo et al. | |
| 2004/0209118 A1 | 10/2004 | Seo et al. | |

FOREIGN PATENT DOCUMENTS

| | | | |
|---|---|---|---|
| EP | 0 953 624 A | | 11/1999 |
| EP | 0953624 A1 | * | 11/1999 |
| EP | 1 146 034 A | | 10/2001 |
| EP | 1 394 617 A | | 3/2004 |
| EP | 1 437 395 A | | 7/2004 |
| JP | 05-025473 | * | 2/1993 |
| JP | 2003-316044 | * | 11/2003 |
| WO | WO 99/54385 A | | 10/1999 |
| WO | WO 03/000773 A | | 1/2003 |
| WO | WO 2004/037887 A | | 5/2004 |

OTHER PUBLICATIONS

Translation of JP 05-025473, Takuma, Hlrosuke, published Feb. 2, 1993.*
Translation of JP 2003-316044, Nakajima, Yuka, published Nov. 6, 2003.*
Patent Abstracts of Japan, vol. 2003, No. 12, Dec. 5, 2003 (corresponds to JP 2003-316044).
Patent Abstracts of Japan, vol. 2002, No. 5, May 3, 2002 (corresponds to JP 2002-003833).
Patent Abstracts of Japan, vol. 2000, No. 25, Apr. 12, 2001 (corresponds to JP 2001-226331).
Patent Abstracts of Japan, vol. 1996, No. 6, Jun. 28, 1996 (corresponds to JP 8-053397).
Patent Abstracts of Japan, vol. 1996, No. 5, May 31, 1996 (corresponds to JP 8-020771).

* cited by examiner

*Primary Examiner*—Golam M. M. Shameem
*Assistant Examiner*—Susannah Chung
(74) *Attorney, Agent, or Firm*—Sughrue Mion, PLLC

(57) ABSTRACT

A halogenated bisdiarylaminopolycyclic aromatic compound, polymers made therefrom, and polymeric light emitting diode devices using the polymers are described. The halogenated compound is represented by formula (I), wherein Ar and Ar' are each independently substituted or unsubstituted aryl groups and Z is a polycyclic arylene group, wherein at least one of the Ar' groups is a haloaryl group. Devices using polymers prepared from the halogenated compound exhibit improved performance and longer lifetime, presumably as a result of the presence of the geometrically constrained diarylaminopolycyclic aromatic groups in the polymer backbone.

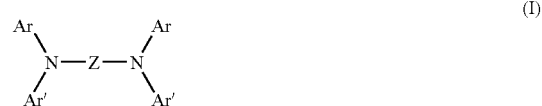

(I)

13 Claims, No Drawings

HALOGENATED BISDIARYLAMINOPOLYCYCLIC AROMATIC COMPOUNDS AND POLYMERS THEREOF

BACKGROUND OF THE INVENTION

The present invention relates to halogenated bisdiarylaminopolycyclic aromatic compounds and polymers thereof and devices made using these polymers.

Conjugated polymers such as polyfluorenes, polythiophenes, polyphenylenes, and poly(p-phenylene vinylenes) are useful as semiconducting layers for light emitting diode devices. For example, fluorene based homopolymers are known to have a high photoluminescent capacity, which is a necessary prerequisite for electroluminescent (EL) applications. However, the homopolymers are not particularly suitable for electroluminescent devices (also known as polymeric light emitting diode devices or pLEDs) because of the inefficiency with which electrons are transferred from the homopolymers to the anode. This sluggishness of electron removal, also known as hole injection, to form radical cations (holes) in the polymer backbone is presumably due to an energy mismatch between the highest occupied molecular orbital (HOMO) of the homopolymer and the work function of the anode. This mismatch has been addressed to some degree by Woo et al. in U.S. Pat. No. 6,309,763 by incorporating triarylamines into the backbone of a polymer that contains structural units of a 9,9-dialkyl-fluorene-2,7-diyl. The presence of triarylamine repeat units have been found to increase the efficiency of hole injection from the anode to the polymer, thereby improving the efficiency of the device. Similarly, Hsieh in U.S. Pat. No. 5,879,821 describes the incorporation of triarylamines into a conjugated polymer to make a more efficient conjugated charge transport polymer.

Radical cations (holes) formed in the polymer backbone as a result of hole injection from the anode combine with radical anions (electrons) formed through electron injection from the cathode to the lowest unoccupied molecular orbital (LUMO) of the polymer to create excited states (excitons). These excitons then undergo radiative relaxation to the ground state and emit light at a wavelength corresponding to the band gap of the polymer. The efficiency and lifetime of the device, therefore, depends on the ability of the injected electrons and holes to "find" each other and recombine to form excitons. Thus, although the introduction of triarylamines into the backbone of conjugated polymers has improved the efficiency of hole injection from the anode to the polymer, there is a further need in the art to improve the efficiency of propagation or transport of holes and electrons through the polymer layer to further increase the lifetime and efficiency of the device.

SUMMARY OF THE INVENTION

The present invention addresses a need in the art by providing in a first aspect a halogenated bisdiarylaminopolycyclic aromatic compound represented by the formula:

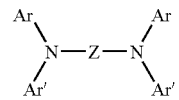

wherein Ar and Ar' are each independently substituted or unsubstituted aryl groups and Z is a polycyclic arylene group, wherein at least one of the Ar' groups is a haloaryl group.

In a second aspect, the present invention is a polymer comprising a backbone containing structural units as shown:

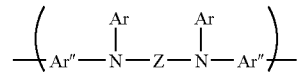

wherein each Ar is independently a substituted or unsubstituted aryl group; each Ar" is a substituted or unsubstituted arylene group; and Z is a polycyclic arylene group.

In a third aspect, the invention is an electronic device comprising a thin film of a polymer disposed between an anode and a cathode, which polymer has structural units as shown:

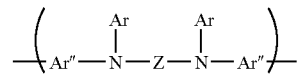

wherein each Ar is independently a substituted or unsubstituted aryl group; each Ar" is a substituted or unsubstituted arylene group; and Z is a polycyclic arylene group.

DETAILED DESCRIPTION OF THE INVENTION

The halogenated bisdiarylaminopolycyclic compound is represented by the following structure:

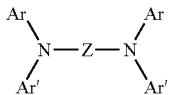

wherein Ar and Ar' are each independently substituted or unsubstituted aryl groups, Z is a polycyclic arylene group, wherein at least one of the Ar' groups is a haloaryl group. Ar and Ar' groups that are bonded to the same nitrogen atom can be bonded to each other to form phenoxazines, phenothiazine, or carbazole groups, but it is preferred that the Ar and Ar' groups are not bonded to each other. More preferably each Ar' is a haloaryl group, more preferably a halophenyl group, and most preferably a bromophenyl group. More preferably, each Ar is a phenyl group, most preferably a substituted phenyl group. By polycyclic arylene group is meant a group having at least one aromatic group that is fused to another ring, which may be aromatic or non-aromatic. These groups are at least divalent—i.e. diyl species. Non-limiting examples of —diyl groups useful in this invention include substituted and unsubstituted groups based upon fluorenes (e.g. fluorenediyl, specifically fluorene-2,7-diyl), naphthalenes, anthracenes, phenanthrenes, tetracenes, perylenes, quinolines, isoquinolines, quinazolines, phenanthridenes, phenanthrolines, phenazines, acridines, dibenzosiloles, phthalazines, dibromocinnolines, quinoxalines, benzoxazoles, benzimidazoles, benzothiophenes, benzothiazoles, carbazoles, benzoxadiazoles, benzothiadiazoles, thieno[3,4-b]pyrazines, [1,2,5]thiadiazolo[3,4-g]-quinoxalines, benzo[1,2-c;3-4c']bis[1,2,5]-thiadiazoles, pyrazino[2,3-g]quinoxalines, benzofurans, indoles, dibenzofurans, dibenzothiophenes, dibenzosiloles, thianthrenes, benzodioxins, benzodioxans, dibenzodioxins, phenazines, phenoxathiins, benzodithiins, benzodioxoles, benzocyclobutenes, dihydrobenzodithiins, dihydrothienodioxins, chromans, isochromans, 9,10-dihydrophenanthrenes, thiazines, phenoxazines, indoles, isoindoles, and dibenzothiophenesulfones.

The halogenated bisdiarylaminopolycyclic aromatic compound can be conveniently prepared in two steps. In a first step, a dibrominated polycyclic aromatic compound can be reacted with a diarylamine in the presence of a palladium catalyst such as palladium(I) acetate, a triarylphospine such as tri-o-tolylphosphine, and a base such as potassium t-butoxide to form an unhalogenated bisdiarylaminopolycyclic aromatic precursor. In a second step the bisdiarylaminopolycyclic aromatic precursor can be converted to the halogenated compound by treatment with a halogenating agent such as N-bromosuccinimide.

The diarylamine is an amine that is bonded to two aryl groups. The aryl groups may be unbonded to each other (for example, diphenylamines, phenyl naphthylamines, and dinaphthylamines) or bonded to each other (to form, for example, phenoxazines, phenothiazines, and carbazoles.) Preferably, the diarylamine is a substituted or unsubstituted diphenylamine, more preferably a monosubstituted diphenylamine as illustrated:

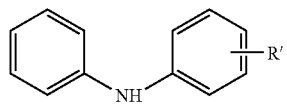

where R' is a substituent that is preferably meta or para to the amine group. R' is preferably a $C_1$-$C_{20}$ alkyl group, a carbo-$C_1$-$C_{20}$-alkoxy group, a $C_1$-$C_{20}$-alkoxy group, or a
$C_6$-$C_{40}$ aryl group more preferably methyl, ethyl, carbomethoxy, or carboethoxy, most preferably methyl. It is also preferred that R' is not bromo.

As used herein, "polycyclic aromatic compound" is used to describe a compound containing at least one aromatic group that is fused to another ring, which may be aromatic or non-aromatic. For the purposes of this invention, biphenyl is not a polycyclic aromatic compound because the two phenyl groups are not fused. The dibrominated polycyclic aromatic compound may, in addition to the bromine groups, contain additional substitution, but is preferably otherwise unsubstituted. Examples of suitable dibrominated polycyclic aromatic compounds include dibromofluorenes, dibromonaphthalenes, dibromoanthracenes, dibromophenanthrenes, dibromotetracenes, dibromoperylenes, dibromoquinolines, dibromoisoquinolines, dibromoquinazolines, dibromophenanthridenes, dibromophenanthrolines, dibromophenazines, dibromoacridines, dibromodibenzosiloles, dibromophthalazines, dibromocinnolines, dibromoquinoxalines, dibromobenzoxazoles, dibromobenzimidazoles, dibromobenzothiophenes, dibromobenzothiazoles, dibromocarbazoles, dibromobenzoxadiazoles, dibromobenzothiadiazoles, dibromothieno[3,4-b]pyrazines, dibromo[1,2,5]thiadiazolo[3,4-g]-quinoxalines, dibromobenzo[1,2-c;3-4c']bis[1,2,5]-thiadiazoles, dibromopyrazino[2,3-g]quinoxalines, dibromobenzofurans, dibromoindoles, dibromodibenzofurans, dibromodibenzothiophenes, dibromodibenzosiloles, dibromothianthrenes, dibromobenzodioxins, dibromobenzodioxans, dibromodibenzodioxins, dibromophenazines, dibromophenoxathins, dibromobenzodithiins, dibromobenzodioxoles, dibromobenzocyclobutenes, dibromodihydrobenzodithiins, dibromodihydrothienodioxins, dibromochromans, dibromoisochromans, dibromo-9,10-dihydrophenanthrenes, dibromothiazines, dibromophenoxazines, dibromoindoles, dibromoisoindoles, and dibromodibenzothiophenesulfones.

Preferred dibrominated polycyclic aromatic compounds include 2,7-dibromo-9,9-dioctylfluorene, 2,7-dibromo-9,9-dihexylphenylfluorene, 2,7-dibromo-9,9-bis(4-hexyloxyphenyl)fluorene, 4,7-dibromo-2,1,3-benzothiadiazole, 5,8-dibromoquinoxaline, 1,4-dibromonaphthalene, and 9,10-dibromoanthracene.

The halogenated bisdiarylaminopolycyclic aromatic compound can be monohalogenated or polyhalogenated, and is preferably dihalogenated, more preferably dibrominated. The dibrominated bisdiarylaminopolycyclic aromatic compound can be prepared by reacting a monosubstituted diarylamine with the dibromopolycyclic aromatic compound as previously described, followed by treatment with N-bromosuccinimide. Where the diarylamine is a diphenylamine, the 2-step reaction scheme is as follows:

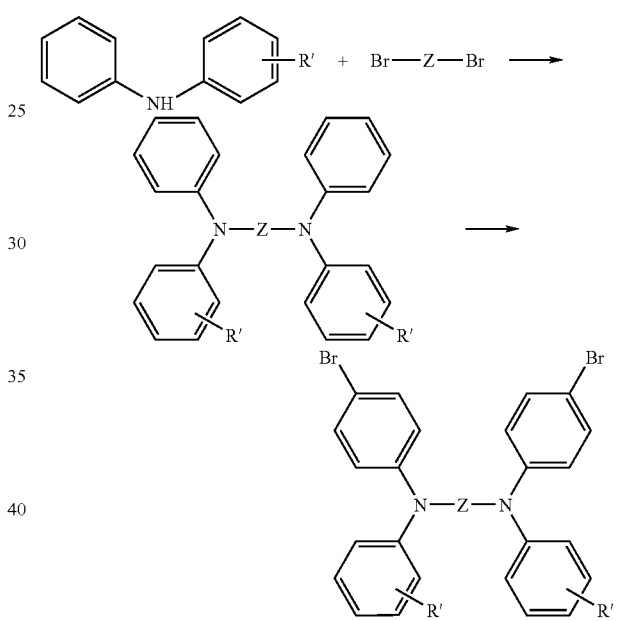

where $ZBr_2$ is previously described. Preferably, Z is 2,1,3-benzothiadiazole-4,7-diyl, 9,9-bis(4-hexyloxyphenyl)fluorene-2,7-diyl, 9,9-dioctylfluorene-2,7-diyl, 9,9-dihexylfluorene-2,7-diyl, naphthalene-1,4-diyl, anthracene-9,10-diyl, or quinoxaline-5,8-diyl.

The monomer is useful as a precursor to a luminescent polymer, preferably a conjugated electroluminescent polymer, which can be a homopolymer, a copolymer, a terpolymer, etc., which contains structural units of the halogenated bisdiarylaminopolycyclic monomer and preferably at least one aromatic comonomer. As used herein, the term "structural units" refers to the remnant of the monomer that appears in the polymer backbone after polymerization. By way of example, a structural unit of an aromatic comonomer such as 1,4-dibromobenzene is a 1,4-phenylene group; a structural unit of a 9,9-disubstituted fluorene comonomer such as a 2,7-dibromo-9,9-disubstituted fluorene, is a 9,9-disubstituted fluorene-2,7-diyl group; a structural unit of a bisdiphenylaminopolycyclic aromatic monomer is illustrated as follows:

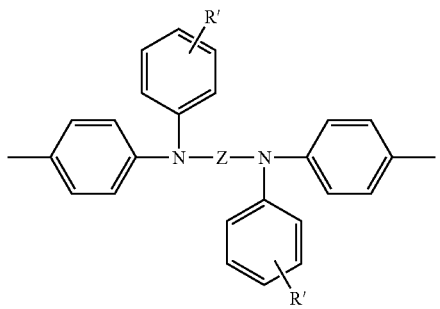

where Z and R' are as previously defined.

The polymer can be prepared by any of a number of means, for example, by a Suzuki coupling reaction, exemplified in U.S. Pat. No. 6,169,163 patent (the '163 patent), column 41, lines 50-67 to column 42, lines 1-24, which description is incorporated herein by reference. In the present case, the Suzuki coupling reaction can be carried out by reacting, in the presence of a palladium catalyst, a phase transfer catalyst such as a quaternary ammonium salt and a strong base, a dibrominated bisdiarylaminopolycyclic aromatic monomer with a diboronated aromatic comonomer, more preferably with a combination of diboronated and dibrominated aromatic comonomers. As used herein, the terms "boronated" and "boronate" refer to to an aromatic fragment or compound that is substituted with a borane group, a boronic acid ester group, or a boronic acid group.

Polymerization can also be carried out by coupling one or more dihalogenated bisdiarylaminopolycyclic aromatic monomers with one or more dihalogenated aromatic compounds in the presence of a nickel salt, as described in the '163 patent, column 11, lines 9-34, which description is incorporated herein by reference.

The aromatic comonomers that can be used to couple with the halogenated bisdiarylaminopolycyclic aromatic monomer is nearly endless but a representative list includes, 1,4-diXbenzenes, 1,3-diXbenzenes, 1,2-diXbenzenes 4,4'-diXbiphenyls, 1,4-diXnaphthalenes, 2,6-diXnaphthalenes, 2,5-diXfurans, 2,5-diXthiophenes, 5,5-diX-2,2'-bithiophenes, 9,10-diXanthracenes, 4,7-diX-2,1,3-benzothiadiazoles, diX triarylamines including N,N-di(4-Xphenyl) anilines, N,N-di(4-Xphenyl)-p-tolylamines; and N-diXphenyl-N-phenylanilines, 3,6-diX-N-substituted carbazoles, 2,7-diX-N-substituted carbazoles, 3,8-diX-dibenzosiloles, 4,7-diX-dibenzosiloles, N-substituted-3,7-dixphenothiazines, N-substituted-3,7-diXphenoxazines, 3,8-diXdibenzosiloles, 4,7-dixdibenzosiloles, diX-N,N,N',N'-tetraaryl-1,4-diaminobenzenes, diX-N,N,N',N'-tetraarylbenzidines, diXarylsilanes, and 2,7-diX-9,9-disubstituted fluorenes, including fluorenes in which the 9,9-substituents combine to form a ring structure, and combinations thereof, where each X is halo or boronate, preferably bromo or chloro or boronate, more preferably bromo or boronate. It is to be understood that the use of the plural (for example, diXbenzenes) indicates that these compounds may include other substituents in addition to the halo or boronate groups.

Particularly suitable aromatic comonomers include 9,9-disubstituted 2,7-fluorenyl diboronates and 9,9-disubstituted 2,7-dihalofluorenes, as shown:

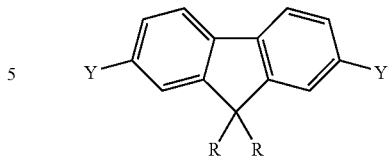

where Y is a halogen atom or a boronate group and each R is a substituent. Preferably, each R is independently $C_4$-$C_{20}$-alkyl, $C_4$-$C_{20}$-alkoxy, $C_7$-$C_{20}$-alkylphenyl, $C_7$-$C_{20}$-alkyloxyphenyl, or $C_6$-$C_{40}$-aryl. More preferably each R is $C_6$-$C_{12}$-alkyl or the following alkyloxyphenyl group:

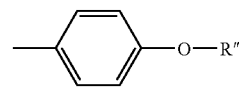

where R" is a $C_6$-$C_{12}$-alkyl group.

The structural units corresponding to the above listed aromatic monomers are 1,4-phenylenes, 1,3-phenylenes, 1,2-phenylenes, 4,4'-biphenylenes, naphthalene-1,4-diyls, naphthalene-2,6-diyls, furan-2,5-diyls, thiophene-2,5-diyls, 2,2'-bithiophene-5,5-diyls, anthracenes-9,10-diyls, 2,1,3-benzothiadiazoles4,7-diyls, N-substituted carbazole-3,6-diyls, N-substituted carbazole-2,7-diyls, dibenzosilole-3,8-diyls, dibenzosilole-4,7-diyls, N-substituted-phenothiazine-3,7-diyls, N-substituted-phenoxazines-3,7-diyls, triarylamine-diyls including triphenylamine-4,4'-diyls, diphenyl-p-tolylamine-4,4'-diyls, and N,N-diphenylaniline-3,5-diyls, N,N,N',N'-tetraaryl-1,4-diaminobenzene-diyls, N,N,N',N'-tetraarylbenzidine-diyls, arylsilane-diyls, and 9,9-disubstituted fluorenes-2,7-diyls.

The concentration of structural units of the bisdiarylaminopolycyclic aromatic monomer in the polymer is application dependent, but can be as little as 1 structural unit per polymer molecule to 100 percent of the polymer backbone.

The polymer of the present invention preferably has a weight average molecular weight $M_w$ of at least 5000 Daltons, more preferably at least 10,000 Daltons, more preferably at least 50,000 Daltons, and most preferably at least 100,000 Daltons; and preferably less than 2,000,000 Daltons, more preferably less than 1,000,000 Daltons. $M_w$ is determined using gel permeation chromatography against polystyrene standards.

The polymer of the present invention can be combined with one or more other polymers to make a blend. Examples of suitable blending polymers include homo- or co-polymers (including terpolymers or higher) of polyacrylates, polymethacrylates, polystyrenes, polyesters, polyimides, polyvinylenes, polycarbonates, polyvinyl ethers and esters, fluoropolymers, polycarbazoles, polyarylene vinylenes, polyarylenes, polythiophenes, polyfurans, polypyrroles, polypyridines, polyfluorenes, and combinations thereof.

The polymer or blend of the present invention can be combined with a sufficient amount of one or more solvents (hereinafter "solvent") to make a solution which is useful, for example, as an ink. The amount of solvent varies depending upon the solvent itself and the application, but is generally used at a concentration of at least 80 weight percent, more preferably at least 90 weight percent, and most preferably at least 95 weight percent, based on the weight of the luminescent polymer, the optional additives or modifiers, and the solvent.

Examples of suitable solvents for the polymer include toluene, di- and trialkylbenzenes including $C_{1-12}$-alkyl benzenes, xylenes, mesitylene, cyclohexylbenzene, and diethylbenzene; furans including tetrahydrofuran and 2,3-benzofuran; 1,2,3,4-tetrahydronaphthalene; cumene; decalin; durene; chloroform; limonene; dioxane; alkoxybenzenes including anisole, and methyl anisoles; alkyl benzoates including methyl benzoate; biphenyls including isopropyl biphenyl; pyrrolidinones including cyclohexylpyrrolidinone; imidazoles including dimethylimidazolinone; and fluorinated solvents; and combinations thereof More preferred solvents include $C_{1-8}$-alkyl benzenes, cyclohexylbenzene, xylenes, mesitylene, 1,2,3,4-tetrahydronaphthalene, methyl benzoate, isopropyl biphenyl, and anisole, and combinations thereof.

In a typical application, the ink formulation can be deposited on a substrate such as indium-tin-oxide (ITO) glass having a hole transporting material disposed thereon. The solvent is then evaporated, whereupon the ink forms a thin film of the luminescent polymer. The film is especially useful as a charge injection layer, a charge transporting layer, a charge blocking layer, or an emissive layer for an organic light-emitting diode (OLED) device, which can be used to make a display such as a self-emissive flat panel display. The film is also useful in other electronic devices including light sources, photovoltaic cells, chemosensors, biosensors, and field effect transistor devices.

The preferred polymer of the present invention results in pLEDs with improved efficiency and longer lifetime. Though not bound by theory, it is believed that this improved performance is due to an increase in electron delocalization resulting from the presence of the geometrically constrained bis-diarylaminopolycyclic aromatic structural groups in the conjugated polymer backbone. In addition to improved performance, it has been surprisingly discovered that the light emissive properties of the polymer can be tuned by varying the polycyclic group that bonds to the diarylamino groups. For example, conjugated polymers containing diphenylaminofluorene and diphenylaminonaphthalene structural units emit a blue color; conjugated polymers containing diphenylaminoanthracene structural units emit a green color; and conjugated polymers containing diphenylaminobenzothiadiazole structural units emit a red color.

The following examples are for illustrative purposes only and are not intended to limit the scope of the invention. Polymer preparation was carried out using CMOS™ toluene and precipitation of the polymer was carried out using CMOS™ methanol. (CMOS is a trademark of J. T. Baker.)

EXAMPLE 1

Preparation of 4,7-bis(N-(4-bromophenyl)-N-p-tolylamino)-2,1,3-benzothiadiazole

A. Preparation of 4,7-bis(N-phenyl-N-p-tolylamino)-2,1,3-benzothiadiazole

Palladium acetate (0.18 g, 0.8 mmol) and tri-o-tolylphosphine (0.49 g, 1.6 mmol) were dissolved in toluene (25 mL). The solution was stirred at room temperature for 15 minutes, whereupon 4,7-dibromo-2,1,3-benzothiadiazole (2.94 g, 10 mmol), 4-methyldiphenylamine (5.0 g, 27.3 mmol) and potassium t-butoxide (3.84 g, 40 mmol) were added. The mixture was refluxed under nitrogen overnight, then cooled to room temperature. Water (~20 mL) was slowly added to the mixture and the organic portion was extracted with several portions of toluene. The combined organic extracts were washed with brine, then dried over magnesium sulfate. Solvent was removed in vacuo, and the residue was redissolved in a 1:1 v/v mixture of toluene and hexane and passed through a silica gel column. Recrystallization from ethanol gave the title compound as a deep red solid (1.2 g).

B. Preparation of 4,7-bis(N-(4-bromophenyl)-N-p-tolylamino)-2,1,3-benzothiadiazole A solution of N-bromosuccinimide (0.8 g, 4.5 mmol) in DMF (5 mL) was added to a solution of 4,7-bis(N-phenyl-N-p-tolylamino)-2,1,3-benzothiadiazole (1.1 g, 2.2 mmol) in DMF (10 mL) at room temperature. The reaction mixture was stirred at room temperature for 2 hours, whereupon water (~200 mL) was added to precipitate the product. The precipitate was collected and washed with water, then methanol. The crude product was redissolved in toluene (~10 mL) and precipitated in methanol (~200 mL). The red product was collected by filtration and recrystallized from DMF to give the title compound as a deep red product (1.0 g).

EXAMPLE 2

Preparation of 2,7-Bis(4-methyl-4'-bromo-diphenylamino)-9,9-dioctylfluorene Monomer A. Preparation of 2,7-Bis(4-methyldiphenylamino)-9,9-dioctyfluorene Pd(II) acetate (0.90 g, 4 mmol) and tri-o-tolylphosphine (2.435 g, 8 mmol) were stirred at room temperature in anhydrous toluene (125 mL) for 15 minutes, whereupon 2,7-dibromo-9,9-dioctylfluorene (27.4 g, 50 mmol), 4-methyldiphenylamine (22.91 g, 125 mmol), and sodium-t-butoxide (19.75 g) were added. The mixture was heated to reflux under nitrogen overnight, then cooled to room temperature, then a first portion of water (~100 mL) was added slowly followed by further dilution with water (~200 mL). The aqueous phase was then separated from the organic phase and the solvent was removed in vacuo. The residue was redissolved in toluene (~100 mL) and the solution was passed through an alumina column. The product was concentrated in vacuo and precipitated from methanol. The crude product was recrystallized from p-xylene as white crystals, which were redissolved in ~100 mL of toluene. The solution was passed through a neutral Al column with toluene and the collected solution was concentrated to ~50-100 mL, then poured into stirred methanol (~250 mL) to precipitate the product. The product was collected and dried in vacuo at room temperature for 18 hours. A white product (25.0 g) was obtained that showed a purity of 99.9 percent by HPLC.

B. Preparation of 2,7-Bis(4-methyl-4'-bromo-diphenylamino)-9,9-dioctylfluorene Monomer A solution of N-bromosuccinimide (5.91 g, 33.2 mmol) dissolved in DMF (~20 mL) was added at −10° C. with stirring to a solution containing 2,7-bis(4-methyldiphenylamino)-9,9-dioctylfluorene (12.5 g, 16.6 mmol) dissolved in methylene chloride (95 mL). Stirring continued for 3.5 hours, after which time cold methanol (~150 mL) was added to the reaction mixture. The mixture was then poured over more cold methanol (~300 mL) and stirred. The crude product was filtered and washed with methanol, then recrystallized from p-xylene to yield a product having a purity by HPLC of 99.45 percent. Redissolution in toluene and reprecipitation in methanol followed by drying in vacuo at 30° C. for 20 hours gave 12.1 g of a white solid having a purity of 99.47 percent.

EXAMPLE 3

Preparation of 1,4-Bis(4-methyl-4'-bromo-diphenylamino)naphthalene Monomer

A. Preparation of 1,4-Bis(4-methyldiphenylamino)naphthalene

Pd(II) acetate (78 mg, 0.35 mmol) and tri-o-tolylphosphine (0.21 g, 0.7 mmol) were stirred at room temperature in anhydrous toluene (50 mL) for 15 minutes, whereupon 1,4-dibromonaphthalene (5.00 g, 17.48 mmol), 4-methyldiphenylamine (6.44 g, 35.13 mmol), and sodium-t-butoxide (4.20 g, 43.7) were added. The mixture was heated to reflux under nitrogen overnight, then cooled to room temperature, whereupon HCl (~20 mL) was added slowly. The mixture was filtered and the filtrate was passed through a basic alumina column. The toluene was removed to yield an orange solid. The solid was recrystallized from hexanes to yield a tan solid 5.3 g (62 percent).

B. Preparation of 1,4-Bis(4-methyl-4'-bromo-diphenylamino)naphthalene

A solution of N-bromosuccinimide (2.90 g, 16.3 mmol) dissolved in DMF (~20 mL) was added at −10° C. with stirring to a solution containing 1,4-bis(4-methyldiphenylamino) naphthalene (4 g, 8.15 mmol) dissolved in methylene chloride (60 mL). Stirring continued for 1 hours, after which time water was added to the mixture. The aqueous layer was extracted with methylene chloride (3×100 mL) and the combined organic fractions were washed with water (3×200 mL). The solution was concentrated to ~100 mL and passed through a silica gel column. The initial light yellow fractions were collected and combined. The methylene chloride was removed in vacuo to yield a pale yellow solid (1 g, 19 percent) that is 97.7 percent pure by HPLC-MS.

EXAMPLE 4

Preparation of 9,10-Bis(4-methyl-4'-bromo-diphenylamino)anthracene Monomer

A. Preparation of 9,10-Bis(4-methyldiphenylamino)anthracene

Palladium acetate (0.27 g, 0.4 mmol) and tri-o-tolylphosphine (0.49 g, 1.6 mmol) were dissolved in toluene (150 mL). The solution was stirred at room temperature for 15 minutes, whereupon 9,10-dibromoanthracene (13.44 g, 40 mmol), 4-methyldiphenylamine (18.3 g, 100 mmol) and sodium t-butoxide (15.4 g, 160 mmol) were added. The mixture was refluxed under nitrogen overnight, then cooled to room temperature. Hydrochloric acid (1N) was added slowly to neutralize the solution and 500 mL of methanol was added. The precipitate was collected by filtration and dried in vacuo at room temperature. The solid was dissolved in 1.5 L of toluene, and the resultant solution was passed through a column of acidic alumina and eluted with toluene. The combined toluene solution was concentrated to ~500 mL and poured into 500 mL of methanol to precipitate the crude product as a yellow powder. The crude product was collected by filtration and was washed with methanol. Twice re-crystallization from a mixture of toluene and ethanol afforded 14.1 g of the final product as a yellow powder.

B. Preparation of 9,10-Bis(4-methyl-4'-bromo-diphenylamino)anthracene Monomer 9,10-bis(4-Methyldiphenylamino)anthracene (2.0 g, 3.7 mmol) was dispersed in chlorobenzene (40 mL). The dispersion was heated to reflux to dissolve the solids then cooled to room temperature, whereupon of NBS (1.32 g dissolved in 5 mL of DMF, 7.4 mmol) was added. The mixture was stirred for 1 hour, then heated to reflux to obtain a clear solution. The solution was slowly cooled to room temperature and was maintained at room temperature overnight to yield yellow crystals. The crystals were collected by filtration and washed with a small amount of toluene, then dried in vacuo at 40° C. overnight to give 2.1 g of the final product as yellow crystals. HPLC showed the purity of 99.2 percent.

EXAMPLE 5

Preparation of Light Emitting Copolymer 2,7-Bis (1,3,2-dioxaborolan-2-yl)-9,9-dihexylfluorene (99.9 percent, 8.00 mmol, 3.82 g), 4,7-dibromo-2,1,3-benzothiadiazole (99.9 percent, 3.60 mmol, 1.06 g), bis(4-bromophenyl-4-sec-butylphenyl)amine (99.9 percent, 0.80 mmol, 0.37 g), 2,7-dibromo-9,9-di(4-hexyloxyphenyl)fluorene (99.8 percent, 3.2 mmol, 2.17 g), 4,7-bis(N-(4-bromophenyl)-N-p-tolylamino)-2,1,3-benzothiadiazole (99.2 percent, 0.40 mmol, 0.264 g), aqueous sodium bicarbonate (2M, 17 mL), Aliquat 336™ phase transfer reagent (a trademark of Henkel, 0.8 g), dichlorobis(triphenylphosphine)palladium (5 mg) and toluene (~50 mL), were added to a vessel. The reaction mixture was stirred and heated to reflux under nitrogen for 6 hours, after which a solution of bromobenzene in toluene (0.14 g in ~10 mL) was added with stirring. Mixture was stirred and heated to 95° C. for 15 hours, then allowed to cool to room temperature. The aqueous phase was separated from the organic phase and the organic phase was washed with water (2x~100 mL), then added to an aqueous solution of DDC (3 g in ~60 mL water). This mixture was heated to 85°0 C. and stirred for 18 hours, then cooled. The aqueous phase was separated from the organic phase, which was washed with 2 percent v/v acetic acid (3x~200 mL) then water (2×200 mL). The organic phase was passed through a column of celite (1"), silica (3"), and alumina (1") and eluted with toluene. The collected polymer fractions were combined and the solution concentrated in vacuo to 300 mL. The polymer was precipitated in methanol (~3 L), and the polymer fibers were collected by filtration and dried in vacuo overnight at 50° C. Yield was 4.5 g. $M_w$ as determined by GPC against polystyrene standards=272,800; $M_n$=111,600; polydispersity=2.45.

EXAMPLE 6

Preparation of Light-Emitting Copolymer 2,7-Bis(1,3,2-dioxaborolan-2-yl)-9,9-dioctylfluorene (2.85 g, 5.37 mmol), 2,7-dibromo-9,9-bis(4-hexyloxyphenyl)fluorene (3.06 g, 4,52 mmol), 2,7-bis(4-methyl-4'-bromo-diphenylamino)-9,9-dioctylfluorene (0.73 g, 0.80 mmol), Aliquat™ 336 phase transfer agent (0.91 g), trans-dichloro-bis(triphenylphosphine)palladium (II) (5 mg) were dissolved toluene (50 mL) with stirring in a 250 mL 3-necked flask at room temperature. The reaction mixture was then heated to reflux, whereupon sodium carbonate (2 M, 11.5 mL) was added. The mixture was stirred for about 4.8 hours, then phenyl boronic acid was added (0.22 g) followed by toluene (30 mL), and the reaction mixture was stirred and heated overnight, then allowed to cool. Water (10 mL) was separated from the reaction mixture and the organic phase was washed with additional water (100 mL), then added to an aqueous solution of sodium diethyldithiocarbamate trihydrate (DDC, 3 g dissolved in 30 mL water) and heated and stirred under nitrogen at 85° C. for 4 hours. Water (16 mL) was separated from the polymer solution, and the solution was washed with 2 percent v/v aqueous acetic acid (2×~100 mL), followed by water washings (3×~100 mL). The organic phase containing the polymer product was passed through a column of celite (1"), silica (3"), and alumina (1") and eluted with toluene. The polymer fractions were combined and the solution concentrated in vacuo to produce about a 3 percent w/v solution of polymer in toluene. The product was precipitated into methanol. The polymer was dried overnight in vacuo at 60° C. and the collected fibers (4.3 g) were air covered in Al foil for 24 hours. The fibers were dissolved in toluene (170 mL), then reprecipitated in methanol. Fibers were collected and dried in vacuo as before to yield 4.22 g (84.4 percent yield). GPC analysis of the polymer showed a number average molecular weight ($M_n$) of 103,867 and a weight average molecular weight ($M_w$) of 303,412, and a polydispersity ($M_w/M_n$) of 2.92.

EXAMPLE 6A

Formulation of Light-Emitting Copolymer Compositions Shown in Example 6

Two copolymer solutions were prepared using tetralin as solvent. Lot A copolymer (Example 6 composition with Mw=311,000) was mixed with tetralin to make a 0.8% solution by weight, prepared by adding the copolymer to tetralin in a vial, then capping and heating the vial at 60° C. until the copolymer fully dissolved. The solution was then allowed to cool to room temperature. The viscosity of this solution was measured using a cone-and-plate rheometer at 25° C. and reported as the average value over the shear range of 600-1000/s. The viscosity was 7.99 cP. Lot B, a second 0.8% by weight formulation, was made in similar fashion using an Example 6 copolymer lot with a higher molecular weight (Example 6 composition with Mw=438,000). The viscosity of the second solution was measured as 10.7 cP. Using the simple rule of mixtures, the two solutions were blended on the basis of viscosity to give a final solution with a target viscosity of 9.0 cP. (See Equation 1) The calculation predicted a blend ratio of 62.82% of lot A solution and 37.18% of lot B solution. The two solutions were mixed for a short time and the viscosity measured again, giving 9.01 cP, in very good agreement with the prediction. (Table 1)

$$\eta_T = \eta_A * w_A + \eta_B * w_B = \eta_A * w_A + \eta_B * (1-w_A) \qquad \text{Equation 1}$$

Where $\eta_T$=target viscosity, $\eta_A$=viscosity of solution of polymer lot A, $w_A$=weight fraction of solution of polymer lot A, $\eta_B$=viscosity of solution of polymer lot B, $w_B$=weight fraction of solution of polymer lot B A similar experiment was done using 1.0% by weight solutions of the same polymer lots. (Table 1) In this experiment the final target viscosity was 12 cP at 25° C. The viscosity of the 1.0% formulation of lot A was 10.59 cP and for lot B was 15.24 cP. The calculation predicted a blend ratio of 69.68:30.32 respectively. The formulations were combined as such and the viscosity of the blended formulation measured 12.04 cP, again in good agreement with the prediction.

TABLE 1

Formulation Parameters for Example 6 Light-emitting Copolymer

| Polymer Lot | Blend Ratio (A:B) | Concentration | Solvent | Viscosity | Blend Target |
|---|---|---|---|---|---|
| A | | 0.80% | Tetralin | 7.994 | |
| B | | 0.80% | Tetralin | 10.7 | |
| A | | 1.00% | Tetralin | 10.59 | |
| B | | 1.00% | Tetralin | 15.24 | |
| | 62.82:37.18 | 0.80% | Tetralin | 9.01 | 9.00 cP |
| | 69.68:30.32 | 1.00% | Tetralin | 12.04 | 12.00 cP |

EXAMPLE 7

Preparation of Light-Emitting Copolymer 2,7-Bis(1,3,2-dioxaborolan-2-yl)-9,9-dioctylfluorene (2.99 g, 5.65 mmol), 2,7-dibromo-9,9-bis(4-hexyloxyphenyl)fluorene (3.52 g, 5.19 mmol), 1,4-(4-methyl-4'-bromo-diphenylamino)naphthalene (0.40 g, 0.45 mmol), Aliquat™ 336 phase transfer agent (0.85 g), trans-dichloro-bis(triphenylphosphine)palladium (II) (4 mg) were dissolved in toluene (50 mL) with stirring in a 250 mL 3-necked flask at room temperature. The reaction mixture was then heated to reflux, whereupon sodium carbonate (2 M, 11.5 mL) was added. The mixture was stirred for about 24 hours, then phenyl boronic acid was added (0.50 g) and the reaction mixture was stirred and heated overnight. The mixture was transferred to a 500 mL round bottom flask and an aqueous solution of DDC (10 g dissolved in 150 mL water) and was heated and stirred under nitrogen at 80° C. for 24 hours.

Water was separated from the polymer solution, and the solution was washed with 2 percent v/v aqueous acetic acid (3×300 mL), followed by water washings (1×300 mL). The polymer was precipitated from methanol (2 L), collected by filtration and washed with methanol. Excess methanol was removed in vacuo and the polymer was dissolved in toluene (500 mL). The solution was passed through a column packed with silica gel, and the polymer was eluted with toluene. The polymer containing fractions were concentrated to ~200 mL, the polymer was precipitated from methanol (2 L), collected by filtration, and washed with methanol. Fibers were collected and dried in vacuo at 60° C. to yield 4.5 g (90 percent) of material. GPC analysis of the polymer showed a number average molecular weight ($M_n$) of 32,118 and a weight average molecular weight ($M_w$) of 95,509, and a polydispersity ($M_w/M_n$) of 2.97.

EXAMPLE 7A

Preparation of Light-Emitting Copolymer—Alternate Work-ups 2,7-Bis(1,3,2-dioxaborolan-2-yl)-9,9-dioctylfluorene (17.09 g, 32.22 mmol), 2,7-dibromo-9,9-bis(4-hexyloxyphenyl)fluorene (18.32 g, 27.11 mmol), 2,7-bis(4-methyl4'-bromo-diphenylamino)-9,9-dioctylfluorene (4.37 g, 4.79 mmol), Aliquat™ 336 phase transfer agent (4.76 g), trans-dichloro-bis(triphenylphosphine)palladium (II) (21.2 mg) were dissolved in toluene (300 mL) with stirring in a 1000 mL 3-necked flask at room temperature. Sodium carbonate (2 M, 67 mL) was added to the solution and the reaction mixture was then heated to reflux. The mixture was stirred for 2.2 hours, then phenyl boronic acid was added (1.2 g) followed by toluene (130 mL), and the reaction mixture was stirred and heated overnight, then allowed to cool. Water (60 mL) was separated from the reaction mixture and the organic phase was washed with additional water (400 mL), then added to an aqueous solution of sodium diethyldithiocarbamate trihydrate (DDC, 15 g dissolved in 150 mL water) and heated and stirred under nitrogen at 85° C. overnight. Water (15 mL) was separated from the polymer solution, and the solution was washed with 2 percent v/v aqueous acetic acid (2×~500 mL), followed by water washings (3×~500 mL). Polymer solution was diluted to 3 L to give a 1% crude polymer solution. 1 L of polymer solution was worked up via a standard procedure.

2 L of the polymer solution were used as the starting material for a comparison of alternate work-ups.

Standard Polymer Workup

The organic phase containing the polymer product was reduced in volume to a 3 percent w/v solution and was precipitated into methanol. Fibers were collected (9.4 g) and dried in vacuo at 60° C. overnight. The fibers were dissolved in toluene (500 mL) and the polymer solution was passed through a column of silica (6"), and alumina (2") and eluted with toluene. The polymer fractions were combined and the solution concentrated in vacuo to produce about a 3 percent w/v solution of polymer in toluene. The product was precipitated into methanol. Fibers were collected and dried in vacuo as before to yield 8.43 g (84.3 percent yield). GPC analysis of the polymer showed a number average molecular weight ($M_n$) of 155,000 and a weight average molecular weight ($M_w$) of 387,000 and a polydispersity ($M_w/M_n$) of 2.49. The final polymer from the standard work up is used as a control for the polymer solution purified via diafiltration.

Diafiltration Work-up

DIAFILTRATION EQUIPMENT: The Diafiltration equipment for this example consisted of a pump, solution reservoir, and diafiltration membrane. Valves were positioned at various points to manipulate pressure, flow rate, and flow direction. The membrane consisted of a 20 inch long ceramic column, approximately 1.25 inches in diameter, with 37 "flow channels" running longitudinally through the column. Nominal pore size for the walls of the column was 100 nm. A ~2 L reservoir, with a continuous nitrogen purge, was used to hold the sample solution.

STARTING MATERIAL FOR DIAFILTRATION: The sample solution consisted of ~1.0 w/w % solution of copolymer from Example 7A. Residual water was visually evident in the solution. A portion of the solution was purified using the standard work up procedure (vide supra) to compare with polymer purified via the diafiltration purification process.

DIAFILTRATION: One diafiltration is defined as the point at which the volume of permeate removed is equal to the volume of the initial starting solution. Three diafiltrations were done on the starting solution. Make up toluene was back added to the reservoir in 200 ml increments, after each 200 ml increment of permeate were removed. During each addition, the flow direction was reversed for ~2 minutes. One diafiltration took approximately one hour. Samples of permeate and retentate were taken for analysis after each diafiltration.

TESTING: Samples were analyzed using Size Exclusion Chromatography, Neutron Activation Analysis, and device performance testing techniques. Table 1, below, shows a summary of the results for the diafiltration process. Table 2, below, shows a comparison of results for polymer that was isolated from a 3× diafiltered solution and a solution passed through a column packed with adsorbent.

TABLE 1

Test results

| Solution Samples | Mw (K Da) | Mw/Mn | Cl (ppm) | Na (ppm) | Br (ppm) | K (ppm) | Pd (ppm) | Efficiency (Cd/A @ 1000 nits) |
|---|---|---|---|---|---|---|---|---|
| 0× Retentate* | 342 | 3.39 | 1.5 | 62.0 | 29.0 | <2.0 | 1.20 | 0.00 |
| 1× Retentate | 349 | 2.95 | 0.8 | 6.8 | 3.5 | <0.5 | 0.40 | 2.54 +/− 0.6 |
| 3× Retentate | 376 | 2.54 | 0.8 | 5.0 | 2.4 | <0.5 | <0.1 | 2.56 +/− 0.3 |
| 1× Permeate | 302 | 4.52 | n/a | n/a | n/a | n/a | n/a | n/a |
| 2× Permeate | 213 | 3.86 | n/a | n/a | n/a | n/a | n/a | n/a |
| 3× Permeate | 233 | 3.38 | n/a | n/a | n/a | n/a | n/a | n/a |

*0× Retentate represents a sample taken after the solution was allowed to recirculate through the diafiltration equipment for ~10 minutes without allowing any actual diafiltration to occur.

TABLE 2

Comparison of isolated polymer samples after adsorbent column purification or diafiltration purification.

| Polymer Samples | Mw (K Da) | Mw/Mn | Cl (ppm) | Na (ppm) | Br (ppm) | K (ppm) | Pd (ppm) | Efficiency (Cd/A @ 1000 nits) |
|---|---|---|---|---|---|---|---|---|
| Control* | 370 | 3.13 | n/a | n/a | n/a | n/a | n/a | 0.00 |
| Purified via Diafiltration | 413 | 2.40 | 4.00 | 35.00 | 22.00 | <2.0 | <1.0 | 2.60 +/− 0.1 |
| Purified via Standard Work up Process | 387 | 2.49 | 3.00 | 51.00 | 20.00 | <2.0 | <1.0 | 2.89 +/− 0.2 |

*Control represents polymer prior to diafiltration or standard work up process

ANALYSIS: The tables clearly show that diafiltration is a useful technique for reducing polydispersity. In this case, a 25% reduction occurred after three diafiltrations. This reduction was achieved by removing polymer of molecular weights of less than or equal to 302 KDaltons. A substantial drop in sodium level is achieved after one diafiltration.

Comparison of three diafiltrations to purification via the standard work up process (Table 2) shows that the two techniques yield approximately the same results. In addition, when comparing the 3× diafiltered solution sample of Table 1 to the corresponding solid polymer sample in Table 2, it is evident that the polymer isolation process yields still further narrowing of the polydispersity.

EXAMPLE 8

Preparation of Light-Emitting Copolymer Using 9,10-Bis(4-methyl4'-bromo-diphenylamino)anthracene Monomer 2,7-Bis(1,3,2-dioxaborolan-2-yl)-9,9-dihexylfluorene (2.91 g, 6.12 mmol), 2,7-dibromo-9,9-bis(4-hexyloxyphenyl)fluorene (3.66 g, 5.40 mmol), 9,10-bis(4-methyl-4'-bromo-diphenylamino)anthracene (0.42 g, 0.60 mmol), Aliquat™ 336 phase transfer agent (1.22 mL), and trans-dichloro-bis(triphenylphosphine)palladium (II) (4.3 mg) were dispersed in toluene (75 mL) with stirring in a 250 mL 3-necked flask at room temperature. Sodium carbonate aqueous solution (2 M, 11.5 mL) was then added and the reaction mixture was stirred and heated at 98° C. under nitrogen for 6 hours. A solution of bromobenzene in toluene (0.04 g in ~10 mL) was then added and heating and stirring were continued for 16 hours, after which phenylboronic acid (0.3 g dissolved in 10 mL of THF) was added. Heating and stirring were continued for another 16 h. Upon cooling to room temperature, the aqueous phase was separated from the organic phase, which was washed with water (2×~100 mL), then added to an aqueous solution of DDC (5 g in 100 mL of water). This mixture was heated to 85° C., stirred for 18 hours, then cooled. The aqueous phase was separated from the organic phase, which was washed with 2 percent v/v acetic acid (3×~200 mL) then water (2×200 mL). The organic phase was passed through a column of celite (1"), silica (3"), and alumina (1") and eluted with toluene. The collected polymer fractions were combined and the solution was concentrated in vacuo to 300 mL. The polymer was precipitated in methanol (~3 L), and the bright lemon yellow polymer fibers were collected by filtration and dried in vacuo overnight at 50° C. Yield was 4.1 g. $M_w$, as determined by GPC against polystyrene standards=229,800; $M_n$=92,700; polydispersity=2.48.

EXAMPLE 9

Preparation of Red Light Emitting Device Using Ca/Al as Cathode

An 80 nm thick film of PEDOT was spin coated onto a clean ITO substrate. The coated substrate was dried at 200° C. for 15 minutes. A film of the copolymer from Example 5 was then spin coated onto the PEDOT coated substrate as a 3 percent w/v solution and at a spinning speed of ~2500 rpm to product a coating of about 80 nm. The polymer film was dried at 130° C. for ~1 hour. A calcium film (35 μm) was deposited by thermal evaporation in vacuo followed by an evaporated layer of Al (150 nm). The resultant device emitted red light (CIE coordinates x=0.668; y=0.327) under dc voltage driving with a brightness reaching 200 cd/m$^2$ at 6.4 V with a light efficiency of 0.43 cd/A and a brightness reaching 1000 cd/m$^2$ at 10.6 V with a light efficiency of 0.39 cd/A.

EXAMPLE 10

Preparation of Red Light Emitting Device Using LiF/Ca/Al as Cathode

The parameters used to create the device of Example 9 were repeated except that a thin layer of LiF (3 nm) was first deposited on the polymer film, followed by deposition of Ca (10 nm) and Al (150 nm). The resultant device emitted red light (CIE coordinates x=0.666; y=0.320) under dc voltage driving with a brightness reaching 200 cd/m$^2$ at 6.9 V with a light efficiency of 0.40 cd/A and a brightness reaching 1000 cd/m$^2$ at 11.4 V with a light efficiency of 0.34 cd/A.

EXAMPLE 11

Preparation of Blue Light Emitting Device Using LiF/Ca/Al as Cathode

The polymer prepared in Example 6 (52 mg) was dissolved in xylenes (4 mL). The solution was heated to 60° C. and shaken for at least 30 minutes before being filtered through a 0.22 μL syringe. An 80 nm film of 1:16 w/w polyethylenedioxythiophene (PEDOT):polystyrene sulfonic acid (PSS) was deposited on a cleaned indium-tin-oxide (ITO) coated glass substrate and baked at 200° C. for 15 minutes. An 80 nm film of the polymer/xylenes solution (1.3 percent w/v) was spin coated onto the PEDOT:PSS film and the coated substrate was baked at 130° C. under nitrogen for 1 hour. The cathode metals LiF (3 nm), Ca (10 nm), and Al (150 nm) were then vacuum deposited over the polymer film. The resultant device emitted blue light (CIE coordinates x=0.15; y=0.12) under dc voltage driving, and gave an average brightness of 200 cd/m$^2$ at 4.43 volts with an average light efficiency of 2.254 cd/A. At 10 V, the average brightness was measured to be 4352 cd/m$^2$.

EXAMPLE 12

Preparation of Green Light Emitting Device Using Ca/Al as Cathode

An 80 nm thick film of PEDOT was spin coated onto a clean ITO substrate. The coated substrate was dried at 200° C. for 15 minutes. A film of the copolymer of Example 8 was then spun coated onto the PEDOT coated substrate as a 1.3 percent w/v solution and at a spinning speed of ~2500 rpm to produce a coating of about 80 nm. The polymer film was dried at 130° C. for ~1 hour. A calcium film (35 nm) was then deposited by thermal evaporation in vacuo followed by deposition of an evaporated layer of Al (150 nm). The resultant device emitted green light (CIE coordinates x=0.340; y=0.610) under dc voltage driving with a brightness reaching 1000 cd/m$^2$ at 6.5 V with a light efficiency of 3.32 cd/A and a brightness reaching 10000 cd/m$^2$ at 11.3 V with a light efficiency of 4.31 cd/A.

EXAMPLE 13

Preparation of White Light-Emitting Copolymer Using 9,10-Bis(4-methyl-4'-bromo-diphenylamino) anthracene Monomer 2,7-Bis(1,3,2-dioxaborolan-2-yl)-9,9-dihexylfluorene (12.3926 g, 23.366 mmol), 2,7-dibromo-9,9-(bis(4-hexyloxyphenyl)fluorene (12.4740 g, 18.438 mmol), 9,10-bis(4-methyl-4'-bromo-diphenylamino)anthracene (0.0323 g, 0.046 mmol), 3,7-dibromo-N-(4-n-butylphenyl)phenoxazine (2.1895 g, 4.625 mmol), 4,7-bis(2'-bromo-5'-thiophenyl)-2,1,3-benzothiadiazole (0.0106 g, 0.023 mmol), Aliquat™ 336 phase transfer agent (3.1 g), and trans-dichloro-bis(triphenylphosphine)palladium (II) (16.1 mg) were dispersed in toluene (180 mL) with stirring in a 1 L 3-necked flask at room temperature. Sodium carbonate aqueous solution (2 M, 45 mL) was then added and the reaction mixture was stirred and heated at 101° C. under nitrogen for 2.5 hours. A solution of phenylboronic acid (1 g in ~10 mL) was then added and heating and stirring were continued for 20 hours. Upon cooling to room temperature, the aqueous phase was separated from the organic phase, which was washed with water (2×~500 mL), then added to an aqueous solution of DDC (10 g in 50 mL of water). This mixture was heated to 95° C., stirred for 18 hours, then cooled. The aqueous phase was separated from the organic phase, which was washed with 2 percent v/v acetic acid (3×~500 mL) then water (2×500 mL). The organic phase was passed through a column of celite (1"), silica (3"), and alumina (1") and eluted with toluene. The collected polymer fractions were combined and the solution was concentrated in vacuo to 1000 mL. The polymer was precipitated in methanol (~7 L), and light orange polymer fibers were collected by filtration and dried in vacuo overnight at 50° C. Yield was 16.8 g. $M_w$ as determined by GPC against polystyrene standards=206,138; $M_n$=95,600; polydispersity=2.40.

EXAMPLE 14

Preparation of White Light Emitting Device Using LiF/Ca/Al as Cathode

The polymer prepared in Example 13 (75 mg) was dissolved in xylenes (5 mL). The solution was shaken at room temperature overnight before being filtered through a 0.22 μL syringe. An 80 nm film of 1:16 w/w polyethylenedioxythiophene (PEDOT):polystyrene sulfonic acid (PSS) was deposited on a cleaned indium-tin-oxide (ITO) coated glass substrate and baked at 200° C. for 15 minutes. An 80 nm film of the polymer/xylenes solution (1.5 percent w/v) was spin coated onto the PEDOT:PSS film and the coated substrate was baked at 130° C. under nitrogen for 1 hour. The cathode metals LiF (3 nm), Ca (10 nm), and Al (150 nm) were then vacuum deposited over the polymer film. The resultant device emitted white 1snyight (CIE coordinates x=0.371; y=0.355) under dc voltage driving, and gave an average brightness of 1000 cd/m² at 5.83 volts with an average light efficiency of 4.73 cd/A. At 10 V, the average brightness was measured to be 12,890 cd/m².

What is claimed is:

1. A halogenated bisdiarylaminopolycyclic aromatic monomer represented by the following formula

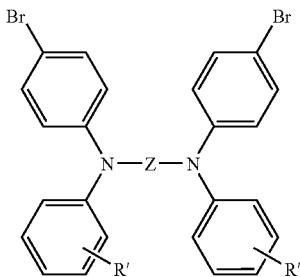

wherein Z is a polycyclic arylene group, and each R' is independently a $C_1$-$C_{20}$ alkyl group, a carbo-$C_1$-$C_{20}$-alkoxy group, a $C_1$-$C_{20}$-alkoxy group, or a $C_6$-$C_{40}$ aryl group.

2. The monomer of claim 1 wherein each R' is methyl, ethyl, carbomethoxy, carboethoxy, methoxy, ethoxy, or hexyloxy, and Z is selected from the group consisting of 2,1,3-benzothiadiazole-4,7-diyls, 9,9-disubstituted fluorene-2,7-diyls, naphthalene-1,4-diyls, anthracene-9,10-diyls, and quinoxaline-5,8-diyls.

3. A polymer comprising a backbone containing structural units of a bisdiarylaminopolycyclic aromatic monomer as shown:

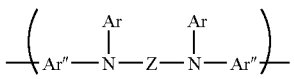

wherein each Ar is independently a substituted or unsubstituted aryl group; each Ar" is a substituted or unsubstituted arylene group; and Z is a polycyclic arylene group; and the polymer backbone further comprises structural units selected from the group consisting of 1,4-phenylenes, 1,3-phenylenes, 1,2-phenylenes, 4,4'biphenylenes, naphthalene-,1,4-diyls, naphthalene-2,6-diyls, furan-2,5 -diy1s, thiophene-2,5 -diyls, 2,2'-bithiophene-5,5 -diyls, anthracenes-9,10-diyls, 2,1,3-benzothiadiazoles-4,7-diyls, N-substituted carbazole-3,6-diyls, N-substituted carbazole-2,7-diyls, dibenzosilole-3,8-diyls, dibenzosilole-4,7-diyls, N-substituted-phenothiazine-3,7-diyls, N-substituted-phenoxazine-3,7-diyls, triarylamine-diyls including triphenylamine-4,4'-diyls, diphenyl-p-tolylamine-4,4'-diyls, and N,N-diphenylaniline-3,5 -diyls, N,N,N',N'-tetraaryl-1,4-diaminobenzene-diyls, N,N,N',N'-tetraarylbenzidine-diyls, arylsilane-diyls, and 9,9-disubstituted fluorenes-2,7-diyls.

4. A polymer comprising a backbone containing structural units of a bisdiarylaminopolycyclic aromatic monomer as shown:

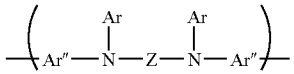

wherein each Ar is independently a substituted or unsubstituted aryl group; each Ar" is a substituted or unsubstituted arylene group; and Z is a polycyclic arylene group, and the polymer backbone further comprises structural units selected from the group consisting of 9,9-bis(4-hexyloxyphenyl)fluorene-2,7-diyl, 9,9-dioctylfluorene-2,7-diyl, 9,9-dihexylfluorene-2,7-diyl, and 2,1,3-benzothiadiazol-4,7-diyl.

5. A polymer comprising a backbone containing structural units of a bisdiarylaminopolycyclic aromatic monomer as shown:

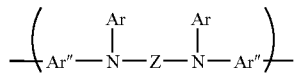

wherein Ar is selected from the group consisting of methyiphenyl, ethylphenyl, carbomethoxyphenyl, carboethoxyphenyl, methoxyphenyl, ethoxyphenyl, and hexyloxyphenyl; Ar" is phenylene; and Z is selected from the group consisting of 2,1,3-benzothiadiazole-4,7-diyls, 9,9-disubstitated fluorene-2,7-diyls, naphthalene-1,4-diyls, anthracene-9,10-diyls, and quinoxaline-5,8-diyls.

6. The polymer of claim 5 wherein Ar is p-methylphenyl and Z is selected from the group consisting of 2,1,3-benzothiadiazole-4,7-diyl, 9,9-bis(4-hexyloxyphenyl)fluorene-2,7-diyl, 9,9-dioctylfluorene-2,7-diyl, 9,9-dihexylfluorene-2,7-diyl, naphthalene-1,4-diyl, anthracene-9,10-diyl, and quinoxaline-5,8-diyl.

7. A composition comprising a mixture of the polymer of claim 3 and a solvent for the polymer suitable for making an ink.

8. A composition comprising a mixture of the polymer of claim 3 and another polymer selected from the group consisting of homo- or co-polymers (including terpolymers or higher) of polyacrylates, polymethacrylates, polystyrenes, polyesters, polyimides, polyvinylenes, polycarbonates, polyvinyl ethers and esters, fluoropolymers, polycarbazoles, polyarylene vinylenes, polyarylenes, polythiophenes, polyfurans, polypyrroles, polypyridines, and polyfluorenes, and combinations thereof.

9. An electronic device comprising a thin film of a polymer disposed between an anode and a cathode, which polymer comprises a backbone containing structural units of a bisdiarylaminopolycyclic aromatic monomer as shown:

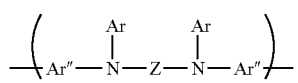

wherein each Ar is independently a substituted or unsubstituted aryl group; each Ar" is a substituted or unsubstituted arylene group; and Z is a polycyclic arylene group, and the polymer backbone further comprises structural units selected from the group consisting of 9,9-bis(4-hexyloxyphenyl)fluorene-2,7-diyl, 9,9-dioctylfluorene-2,7-diyl, 9,9-dihexylfluorene-2,7-diyl, and 2,1,3-benzothiadiazol-4,7-diyl.

10. An electronic device comprising a thin film of a polymer disposed between an anode and a cathode, which polymer comprises a backbone containing structural units of a bisdiarylaminopolycyclic aromatic monomer as shown:

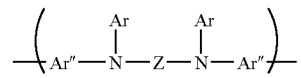

wherein each Ar is independently a substituted or unsubstituted aryl group; each Ar" is a substituted or unsubstituted arylene group; and Z is a polycyclic arylene group; and the polymer backbone further comprises structural units selected from the group consisting of 1,4-phenylenes, 1,3-phenylenes, 1,2-phenylenes, 4,4'-biphenylenes, naphthalene-1,4-diyls, naphthalene-2,6-diyls, furan-2,5-diyls, thiophene-2,5-diyls, 2,2'-bithiophene-5,5-diyls, anthracenes-9,10-diyls, 2,1,3-benzothiadiazoles-4,7-diyls, N-substituted carbazole-3,6-diyls, N-substituted carbazole-2,7-diyls, dibenzosilole-3,8-diyls, dibenzosilole-4,7-diyls, N-substituted-phenothiazine-3,7-diyls, N-substituted-phenoxazines-3,7-diyls, triarylamine-diyls including triphenylamine-4,4'-diyls, diphenyl-p-tolylamine-4,4'-diyls, and N,N-diphenylaniliine-3,5-diyls, N,N,N',N'-tetraaryl-1,4-diaminobenzene-diyls, N,N,N',N'-tetraarylbenzidine-diyls, arylsilane-diyls, and 9,9-disubstituted fluorenes-2,7-diyls.

11. The electronic device of claim 10 wherein Ar is p-methylphenyl, Ar" is phenyl, and Z is selected from the group consisting of 2,1,3-benzothiadiazole-4,7-diyl, 9,9-bis(4-hexyloxyphenyl)fluorene-2,7-diy 1, 9,9-dioctylfluorene-2,7-diyl, 9,9-dihexylfluorene-2,7-diyl, naphthalene-1,4-diyl, anthracene-9,10-diyl, and quinoxaline-5,8-diyl.

12. The monomer of claim 1 wherein Z is selected from the group consisting of 2,1,3-benzothiadiazole-4,7-diyl, 9,9-disubstitated fluorene-2,7-diyls, naphthalene-1,4-diyls, anthracene-9,10-diyls, and quinoxaline-5,8-diyls.

13. An electronic device comprising a thin film of a polymer disposed between an anode and a cathode, which polymer comprises a backbone containing structural units of a bisdiarylaminopolycyclic aromatic monomer as shown:

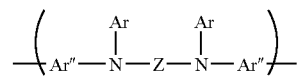

wherein Ar is selected from the group consisting of methylphenyl, ethylphenyl, carbomethoxyphenyl, carboethoxyphenyl, methoxyphenyl, ethoxyphenyl, and hexyloxyphenyl; Ar" is phenylene; and Z is selected from the group consisting of 2,1,3-benzothiadiazole-4,7-diyls, 9,9-disubstitated fluorene-2,7-diyls, naphthalene-1,4-diyls, anthracene-9,10-diyls, and quinoxaline-5,8-diyls.

* * * * *

UNITED STATES PATENT AND TRADEMARK OFFICE
CERTIFICATE OF CORRECTION

| | |
|---|---|
| PATENT NO. | : 7,651,746 B2 |
| APPLICATION NO. | : 10/579215 |
| DATED | : January 26, 2010 |
| INVENTOR(S) | : Michelle Hudack et al. |

It is certified that error appears in the above-identified patent and that said Letters Patent is hereby corrected as shown below:

On the Title Page, please include the Related U.S. Application Data Item (60):

Item (60) Provisional application No. 60/520,070, filed November 14, 2003.

Signed and Sealed this

Eighteenth Day of May, 2010

David J. Kappos
*Director of the United States Patent and Trademark Office*